(12) United States Patent
Ley et al.

(10) Patent No.: US 7,462,489 B2
(45) Date of Patent: Dec. 9, 2008

(54) METHODS FOR IDENTIFYING AND ANALYZING BIOMARKERS FROM PLASMA-DERIVED MICROPARTICLES

(76) Inventors: Klaus F. Ley, 1339 Cottontail La., La Jolla, CA (US) 92037; David M. Smalley, 3182 Saddlebrook La., Charlottesville, VA (US) 22911

( * ) Notice: Subject to any disclaimer, the term of this patent is extended or adjusted under 35 U.S.C. 154(b) by 0 days.

(21) Appl. No.: 11/935,048

(22) Filed: Nov. 5, 2007

(65) Prior Publication Data

US 2008/0171312 A1  Jul. 17, 2008

Related U.S. Application Data

(60) Provisional application No. 60/857,928, filed on Nov. 9, 2006.

(51) Int. Cl.
  *A01N 1/02* (2006.01)
  *A01N 31/00* (2006.01)
  *A01N 33/00* (2006.01)

(52) U.S. Cl. ............... 436/16; 435/2; 436/86; 436/89; 514/2

(58) Field of Classification Search .............. None
  See application file for complete search history.

(56) References Cited

U.S. PATENT DOCUMENTS 5,512,657 A * 4/1996 Van Aken et al. ............ 530/350
2007/0238864 A1 * 10/2007 Ottens et al. ................ 530/413

* cited by examiner

*Primary Examiner*—Herbert J. Lilling
(74) *Attorney, Agent, or Firm*—Feldman Gale P.A.

(57) ABSTRACT

The present invention provides methods for identifying candidate biomarkers in the plasma microparticle proteome. It also provides methods for isolating, identifying, and analyzing microparticles derived from plasma, particularly platelet-poor plasma.

20 Claims, 4 Drawing Sheets

Figure 1

A    Comparative Analysis
     Unlabeled Approach

B    Comparative Analysis
     ICAT-labeled Approach

METHODS FOR IDENTIFYING AND ANALYZING BIOMARKERS FROM PLASMA-DERIVED MICROPARTICLES

CROSS-REFERENCE TO RELATED APPLICATIONS

The present application claims the priority benefits of U.S. Provisional Application No. 60/857,928, filed 9 Nov. 2006, which is expressly incorporated fully herein by reference.

BACKGROUND OF THE INVENTION

Plasma contains one of the most complex and useful human proteomes. Detection of proteins within this type of sample is currently an important tool for evaluating the predisposition, presence, and progression of numerous clinical conditions. However, the current methodology of detecting and measuring individual proteins only begins to scratch the surface of its full potential. Today, tests for only about 120 different protein analytes have been approved by the FDA and approval of tests to detect new protein analytes has averaged only about one test per year over the last decade. This represents only an extremely small fraction of the 40,000 different proteins present in normal plasma and another 500,000 proteins which may be present under a variety of clinical conditions. This has led investigators to attempt to develop methods using high-throughput detection methods to identify many more proteins in the plasma. Current methodology, based on 2D gels, liquid chromatography, and/or mass spectrometry, has lead to the detection of about 500 different plasma proteins. However, this appears to be the limit of detection for the analysis of unfractionated plasma due to the limited dynamic range of these analytical methods. Abundant proteins, such as albumin (35-45 mg/ml), fibrinogen (2-6 mg/ml), immunoglobulins (12-18 mg/ml), and transferrin (2-3 mg/ml), interfere with the detection of proteins that may be present at up to 10 orders of magnitude lower concentrations. Removal of the ten most abundant proteins only increases the sensitivity by one order of magnitude, still leaving most proteins undetected. This has led some to attempts to fractionate the plasma samples to reduce its complexity prior to analysis.

Microparticles (MPs) are small subcellular membranous vesicles released by essentially all cell types, especially when activated or under stress. They include ectosomes, generated from the ectocytosis (or blebbing) of the plasma membrane, and exosomes, released by fusion of intracellular multivesicular endosomes with the cell surface. In plasma, MPs were discovered as a blood component that promotes coagulation due to the presence of anionic phospholipids on their outer surface. These anionic phospholipids, which are mostly phosphatidylserine, are now widely used to detect MPs from blood samples using flow cytometry based on their affinity for fluorescently labeled annexin V. The cellular source of microparticles can be determined by cell-specific markers detected by flow cytometry. For example, MPs with CD41 (Glycoprotein IIb) expression are believed to be generated by platelets. Using this method, microparticles from platelets, erythrocytes, endothelial cells, neutrophils, lymphocytes and even smooth muscle cells have been detected in plasma. In healthy individuals, over 90% of these MPs originate from platelets, and under a wide range of pathological conditions the total number of microparticles and the number originating from various cell population are altered.

Traditionally, the presence of these microparticles in the plasma is considered a sign of cellular activation and/or damage generated by the random blebbing of cell membranes. However, significant evidence has accumulated to indicate that MPs contain a unique set of proteins and inflammatory factors that have important biological functions. For example, a major pathway for the rapid secretion of IL-1β from THP-1 monocytes occurs via MP release in ectosomes, and this could be a general mechanism of release for secreted proteins that lack the conventional signaling peptide for secretory proteins. Researchers using MPs isolated either from plasma or the supernatants of stimulated cells have demonstrated a wide variety of effects on cellular function. These effects of MPs include increased expression of adhesion molecules on endothelial cells and monocytes, stimulation of cytokine release, altering vascular reactivity, inducing angiogenesis, decreasing the response to inflammatory mediators, and promoting fibrin formation. The effects vary depending on the cellular source of the microparticles, the method to generate them and the cells (or tissue) affected. While many groups have studied the effects of these MPs on various cells, the protein composition of plasma MPs was largely unknown except for the presence of a few cell-surface markers. Recently, we analyzed the proteome of platelet-derived microparticles and identified 578 proteins. Many microparticles in plasma are derived from platelets, but it is believed that valuable information resides in plasma microparticles derived from other cells as well.

It is therefore desirable to find methods of identifying biomarkers in plasma microparticles that can be useful for diagnosing various diseases, disorders, and conditions.

SUMMARY OF THE INVENTION

The present invention provides methods for isolating, identifying, and analyzing microparticles derived from plasma, particularly platelet-poor plasma. The present invention further provides methods for identifying and analyzing biomarker components of microparticles, particularly proteins and peptides. In one aspect the peptides are components of larger proteins. Plasma-derived microparticles (MPs) were isolated from human blood of three healthy donors using gel filtration and ultracentrifugation. Platelet-derived MPs were produced from human platelets by incubation with ADP, followed by gel filtration and ultracentrifugation. A fraction of each sample was labeled with the ICAT method (U.S. Pat. No. 6,629,040) and processed using the gel-based protocol using manufactures instructions (Applied Biosystems). Another fraction was run on SDS PAGE, digested with trypsin, and extracted. Both sets of samples were analyzed by LC-MS on a ThermoFinnigan LTQ mass spectrometer. Peptide identifications were made using a first-pass filtering of standard criteria of cross correlation values >2.0 (+1 charge), 2.2 (+2 charge) and 3.5 (+3 charge) and requiring that all peptides be fully tryptic. The samples were compared using spectral counts or ICAT. At least twenty-six proteins were identified herein which are found in plasma-derived, but not in platelet-derived MPs, and three more that were much more abundant in plasma-derived MPs.

The present invention is useful for identifying, measuring, and analyzing additional biomarkers from blood other than those specifically disclosed herein. In one aspect, these biomarkers are useful for identifying disease states in subjects, for monitoring progression of diseases and disorders, and for monitoring response to treatment. The present invention is also useful for identifying a predisposition to a disease or disorder by detecting a biomarker of the invention associated with said disease or disorder. The present invention is also useful for identifying and comparing proteins and peptides from normal and diseased tissues other than blood. The present invention is also useful for identifying biomarkers that have medical prognostic value for patients receiving treatment for a disease to determine how well the treatment is working.

In normal humans, over 90% of microparticles are from platelets. Therefore, platelet microparticles represent a "background" and are less likely to contain useful information. To this end, the present invention provides in an aspect for subtracting the platelet microparticle proteome from the plasma microparticle proteome.

BRIEF DESCRIPTION OF THE DRAWINGS

FIG. 2, comprising parts A and B, illustrates a sample section of a 2D gel and analysis of the data as presented by MSight®. Files generated by the mass spectrometer were converted into .mzXML files and imported into MSight®. A) Sample portion of intensity plot for M/Z between 810 to 1020 and retention time from 90 to 145 min. B) Peptides were annotated for relative quantitation and identification. While most spots appears as pairs of equal intensity, there are several that do not (6, 9, 29, etc.).

DETAILED DESCRIPTION OF THE INVENTION

Thus, in an embodiment, the present invention provides a novel method of identifying candidate biomarkers in the plasma microparticle sub-proteome, comprising:
  (a) isolating proteins from blood plasma microparticles obtained from at least one blood sample from a case and at least one blood sample from a control;
  (b) identifying the proteins;
  (c) applying a statistical test to measure the abundance of each protein identified; and,
  (d) determining the presence of positive and negative biomarkers by comparing the abundance of each protein identified in at least one case blood sample with the abundance of the same protein in at least one control blood sample.

In another embodiment, the present invention provides a novel method wherein isolating proteins (a), further comprises:
  (e) isolating a plasma microparticle-enriched fraction from a blood sample;
  (f) purifying plasma microparticles from the enriched fraction; and,
  (g) isolating proteins from the purified microparticles.

In another embodiment, the present invention provides a novel method wherein isolating a plasma microparticle-enriched fraction (e), comprises:
  (h) separating platelet-poor plasma (PPP) from a blood sample; and,
  (i) fractionating by size to obtain a plasma microparticle-enriched fraction.

In another embodiment, the present invention provides a novel method wherein purifying plasma microparticles (f), comprises:
  (j) fractionating the plasma microparticle-enriched fraction to obtain plasma microparticles.

In another embodiment, the present invention provides a novel method wherein isolating proteins (g), comprises:
  (k) delipidating the resulting plasma microparticles to obtain proteins.

In another embodiment, the present invention provides a novel method, further comprising:
  (l) optionally cleaving the resulting proteins to obtain peptides.

In another embodiment, the present invention provides a novel method wherein (h) separating the plasma microparticle-enriched fraction is performed by centrifugation.

In another embodiment, the present invention provides a novel method, wherein (i) purifying by fractionating by size is performed by running the fractionated plasma microparticles through a size exclusion column.

In another embodiment, the present invention provides a novel method wherein (j) fractionating the PPP is performed by centrifugation.

In another embodiment, the present invention provides a novel method wherein the centrifugation is sufficient to form a pellet comprising: plasma-derived microparticles.

In another embodiment, the present invention provides a novel method wherein (k) delipidating is performed by submitting the plasma microparticles to gel electrophoresis.

In another embodiment, the present invention provides a novel method, wherein the gel electrophoresis is SDS PAGE.

In another embodiment, the present invention provides a novel method wherein (l) cleaving is performed by digesting the delipidated proteins with an appropriate enzyme.

In another embodiment, the present invention provides a novel method wherein the enzyme is trypsin.

In another embodiment, the present invention provides a novel method wherein (b) identifying is performed by sequencing the resulting proteins or peptides.

In another embodiment, the present invention provides a novel method wherein (b) identifying is performed by sequencing the resulting peptides.

In another embodiment, the present invention provides a novel method wherein the sequencing is performed by mass spectrometry.

In another embodiment, the present invention provides a novel method wherein the sequencing is performed by a HPLC-MS/MS.

In another embodiment, the present invention provides a novel method wherein (c) applying a statistical test is performed by using a method selected from: ion current, spectral count, and coverage.

In another embodiment, the present invention provides a novel method wherein the statistical method used is comparing spectral counts between cases and controls.

A protein can be considered a positive biomarker when it shows an increased presence in a case when compared with a control and a protein can be considered a negative biomarker when it shows a decreased presence in a case when compared with a control.

Purifying plasma microparticles is a process wherein abundant plasma proteins (e.g., albumin, fibrinogen, and compliment factors) are suppressed (e.g., either absent or found in low counts in the spectral analysis).

The process of the present invention can further comprise collecting a blood sample from a case and/or control. These blood samples may be drawn fresh via a variety of methods, examples of which include venipuncture, an indwelling venous or arterial catheter, an intraoperative sample, and blood removed from a wound site during or after surgery. Blood may also be obtained from blood banks. It can be desirable to obtain plasma from the sample immediately (e.g., within 24 hours) and processed to obtain MPs. Plasma may also be obtained from plasma or serum banks. The yield of MP proteins from frozen plasma or serum is typically lower than from fresh plasma. However frozen plasma remains a potential sample source.

A case is a subject having a disease, condition or disorder. A control is a subject with demonstrated absence of the disease, condition or disorder. For rare diseases, disorders, and conditions, controls are taken from the general population and matched for known risk factors. If the condition is rare (less than 1 in 100), the proposed method is still useful for discovering biomarkers even when the disease, condition or disorder is not demonstrated to be absent in the controls.

It is expected that the present invention can be used to identify biomarkers in body fluids that include normal tissue samples, diseased tissue samples, biopsies, blood, saliva, feces, semen, tears, cerebrospinal fluid, tears, vaginal lavage fluid, bronchoalveolar lavage fluid, ERCP lavage fluid, and any body fluid other than urine.

Platelet poor plasma (PPP) can be obtained by removal of platelets from plasma. One procedure that has been used to effect this separation is centrifugation. Typically, the blood sample is subjected to centrifugation until a platelet pellet is formed, with the supernatant being the PPP. Other types of separation technologies could be used. For example, one of ordinary skill in the art could envision using the micromachined filtering device of U.S. Pat. No. 6,637,257 to separate the PPP from the blood sample.

Microparticle-containing fractions are collected from a size exclusion column, for example by gel filtration. The presence of microparticles is determined by testing fractions for the presence of proteins. A positive test indicates the presence of a plasma microparticle. Fractions are excluded when the protein content exceeds 100 micrograms per milliliter. Typically, this is determined using a MicroBCA protein assay kit from Pierce Biotechnology but other protein assays will also suffice.

The level of centrifugation necessary to form a pellet comprising plasma microparticles is called ultracentrifugation. Ultracentrifugation is defined as centrifugation generating sedimentation accelerations, also known as g-forces, in access of 10,000 g, where g is the gravitational constant (9.81 m/s$^2$). Typically, 100,000 g are used to sediment MPs.

It can be beneficial to cleave the delipidated proteins in order to simplify their identification. The identification can then be achieved by sampling the peptide fragments of the digested proteins by MS and sequencing them by MS/MS.

Peptides are identified using a statistical algorithm that compares the top 500 peptides compatible with the masses measured to a database based on the human (or other animal) genome. Examples of suitable software include Sequest® and MASCOT®.

Any mass spectrometer sensitive enough to sequence proteins can be used. Examples include the ThermoFinnigan LTQ-FT and the ThermoFinnigan LTQ instrument. Time-of-flight mass spectrometers such as Q-TOF can also be used. Electrospray ionization (ESI) has been used as an ion source, but MALDI and related methods may also be used.

Ion currents are compared by integrating the area under the curve for cases and controls, and forming the ratio. A statistical test is the t test. Spectral counts can be compared with t test followed by Bonferroni correction. Since spectral counts are not normally distributed, non-parametric tests are preferred, such as Wilcoxon rank sum test. One embodiment is contained in a software package called R. Coverage refers to the number of unique peptides per protein, and what percentage of the entire sequence is covered. In general, more unique peptides and higher coverage increase the confidence in protein detection. This is generally used in addition to the XCOR values defined above.

Alternatively, spectral counts for individual peptides or groups of peptides identifying individual proteins or groups of proteins forming functional groups can be tested for differences between cases and controls by using distribution-free methods. One such method is random permutation. To determine false discovery rate, the labels can be removed from cases and controls, and random permutations of the data can be constructed as known in the art. Labels for cases and controls are then attached randomly to these permutations and tested for significance using the Wilcoxon rank sum test or other test known in the art. If the random permutation produces a result with a probability (p) value smaller than that obtained when the cases are compared with the controls, this constitutes a false discovery. The false discovery rate is then determined in analogy to procedures known in the art.

Definitions

In describing and claiming the invention, the following terminology will be used in accordance with the definitions set forth below.

Abbreviations and Acronyms
AIM means Apoptosis Inhibitor in Macrophages
C4BP means Complement Component C4 Binding Protein
ESI means electrospray ionization
FCGBP means Fc fragment of IgG binding protein
ICAT means Isotope-Coded Affinity Tag
LC/MS means liquid chromatography/mass spectrometry
LC/MS means liquid chromatography-tandem mass spectrometry
MALDI means matrix-assisted laser desorption/ionization
MPs means Microparticles
MS/MS means tandem mass spectrometry.
PAGE means Polyacrylamide gel electrophoresis
PBS means Phosphate buffered saline
PPP means Platelet-Poor Plasma
PRP means Platelet-Rich Plasma
SDS means sodium dodecyl sulfate
TOF means time-of-flight
vWF means von Willebrand Factor The articles "a" and "an" are used herein to refer to one or to more than one (i.e., to at least one) of the grammatical object of the article. By way of example, "an element" means one element or more than one element.

As used herein, the term "affected cell" refers to a cell of a subject afflicted with a disease or disorder, which affected cell has an altered phenotype relative to a subject not afflicted with a disease or disorder. Cells or tissue are "affected" by a disease or disorder if the cells or tissue have an altered phenotype relative to the same cells or tissue in a subject not afflicted with a disease or disorder.

As used herein, the term "biologically active fragments" or "bioactive fragment" of the polypeptides encompasses natural or synthetic portions of the full-length protein that are capable of specific binding to their natural ligand or to a new ligand not bound by the intact protein or of performing the function of the protein.

A "biomarker" is a specific biochemical in the body which has a particular molecular feature that makes it useful for measuring the progress of disease or the effects of treatment, or for measuring a process of interest.

A "compound," as used herein, refers to a polypeptide, isolated nucleic acid, chemical, or other agent used, identified, or isolated in the method of the invention.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "case" cell, tissue, sample, or subject is one being examined or treated.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "fragment" or "segment" is a portion of an amino acid sequence, comprising at least one amino acid, or a portion of a nucleic acid sequence comprising at least one nucleotide. The terms "fragment" and "segment" are used interchangeably herein.

The term "microparticle", as used herein, refers to any protein containing particle less than 2 micrometers in diameter with a molecular weight of over 100,000 daltons. These include various lipoproteins and membrane vesicles released from cells (see, for example, Piccin, A. et. al, Blood Reviews 2007, 21, 157-171).

As used herein, a "peptide" encompasses a sequence of 2 or more amino acid residues wherein the amino acids are naturally occurring or synthetic (non-naturally occurring) amino acids covalently linked by peptide bonds. No limitation is placed on the number of amino acid residues which can comprise a protein's or peptide's sequence. Proteins are intact natural or synthetic proteins. Peptides are fragments of proteins (e.g., trypic peptides). Tryptic peptides are peptides resulting from the action of the protease trypsin on natural or synthetic proteins.

"Plurality" means at least two.

The term "purified" relates to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "sample," as used herein, refers preferably to a biological sample from a subject, including, but not limited to, normal tissue samples, diseased tissue samples, biopsies, blood, saliva, feces, semen, tears, cerebrospinal fluid, tears, vaginal lavage fluid, bronchoalveolar lavage fluid, ERCP lavage fluid, and any body fluid other than urine. A sample can also be any other source of material obtained from a subject that contains cells, tissues, or fluid of interest. A sample can also be obtained from cell or tissue culture.

As used herein, the term "secondary antibody" refers to an antibody that binds to the constant region of another antibody (the primary antibody).

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

In one embodiment, the present invention provides methods for isolating microparticles from plasma which has been depleted of platelets. In one embodiment, the present invention provides a method for identifying and analyzing microparticles isolated from plasma. In one aspect, the method provides for isolating microparticles from platelet-poor plasma. In one aspect, the method provides for identifying and analyzing biomarkers associated with microparticles. In one aspect, the biomarkers are proteins and peptides, or homologs or fragments thereof. In one aspect, the presence of a biomarker identified by the methods of the invention, or a difference in the level of the biomarker relative to a normal control level, is indicative of a disease, disorder, or condition. In one embodiment, the present invention provides diagnostic assays for diseases, disorders, and conditions using biomarkers identified by the methods of the invention.

The invention is now described with reference to the following Examples. These Examples are provided for the purpose of illustration only and the invention should in no way be construed as being limited to these Examples, but rather should be construed to encompass any and all variations that become evident as a result of the teaching provided herein.

EXAMPLES

Materials and Methods

Isolation of platelets and platelet-derived MPs. Platelets and platelet-derived MPs were isolated as previously described (see Garcia B A, Smalley D M, Cho H, Shabanowitz J, Ley K, Hunt D F. The Platelet Microparticle Proteome. *J Proteome Res.* 2005; 4: 1516-1521). Briefly, human blood was collected by venipuncture into 1/10 volume of an acid-citrate-dextrose (85 mM trisodium citrate, 83 mM dextrose, and 21 mM citric acid) solution. Platelet-rich plasma (PRP) was obtained by centrifugation at 110×g for 15 minutes. Platelets were pelleted by centrifugation at 710×g for 15 minutes, and the supernatant, platelet-poor plasma (PPP), was retained for isolation of plasma MPs (see below). The platelet pellet was washed three times, resuspended in 10 mL of Tyrode's buffer, and centrifuged one additional time at 110×g to remove remaining red blood cells or debris. To generate platelet-derived microparticles, ADP (10 μM final concentration) was added to the platelet suspension for 10 minutes. Platelets were removed by centrifugation (710×g for 15 minutes) and platelet-derived MPs were pelleted by centrifugation at 150,000×g for 90 minutes at 10° C.

Isolation of plasma-derived MPs. Plasma-derived MPs were isolated by gel filtration chromatography followed by ultracentrifugation. Briefly, the platelet-poor plasma (PPP) generated above was centrifuged an additional two times to remove residual cells and cell debris at 710×g and 25° C. for 15 minutes. This plasma was then applied to a Sephacryl® S-500 HR (GE Healthcare, Piscataway, N.J.) gel filtration column and MP-containing fractions were concentrated by ultracentrifugation at 150,000×g for 90 minutes at 10° C.

Figure 1:
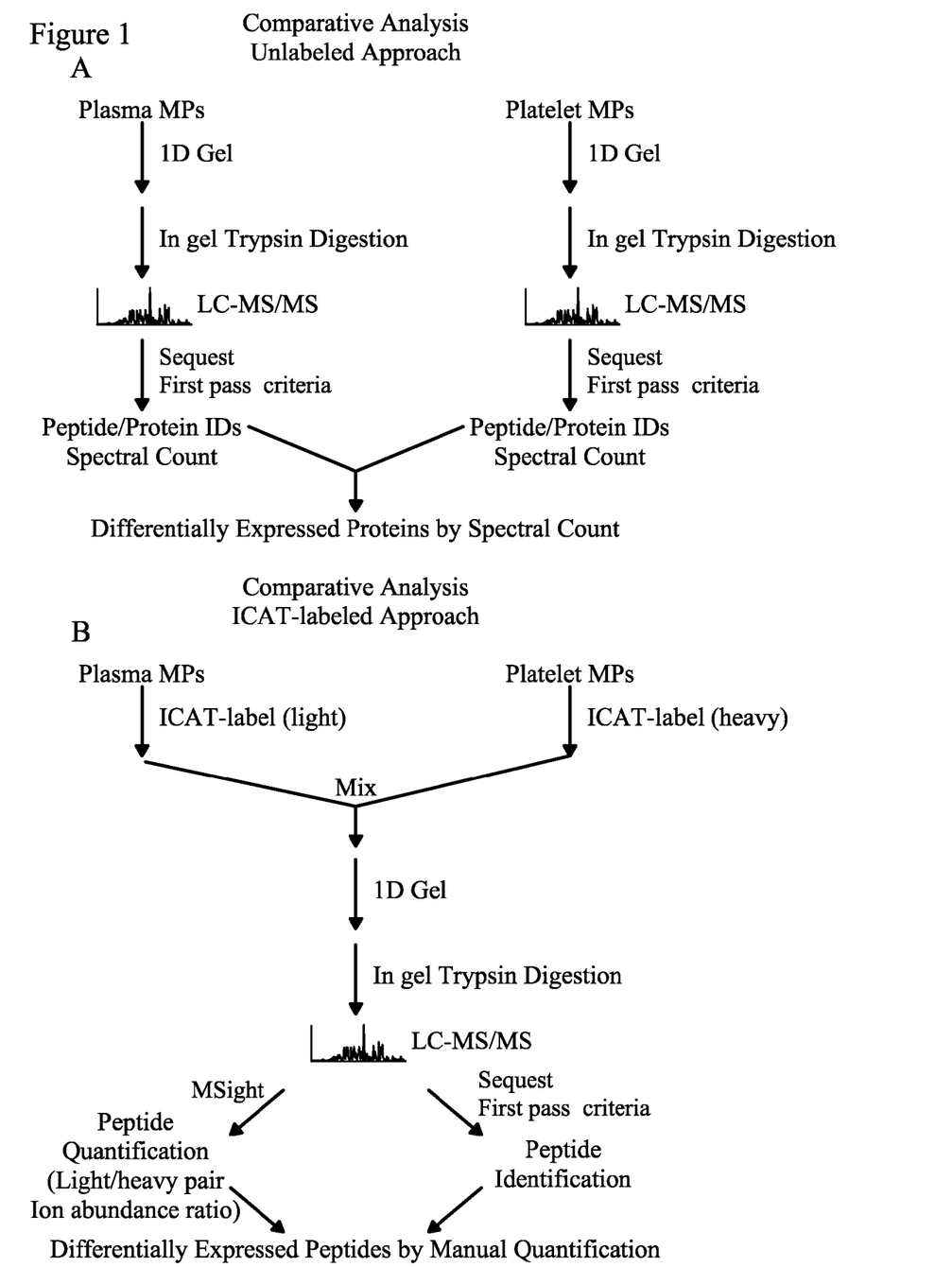
FIG. 1, comprising A and B, provides a schematic representation of a comparative proteomic analysis of plasma MPs and platelet MPs. Two complementary approaches to compare the proteome of plasma and platelet MPs are depicted. A) Comparative analysis of unlabeled proteins based on spectral count. B) Comparative analysis of ICAT-labeled proteins by manual quantitation of labeled peptide ion intensities.

Sample preparation for unlabeled protein analysis. Platelet- and plasma-derived microparticle pellets were processed as depicted in FIG. 1A. MPs were resuspended in a minimal volume of PBS (phosphate buffered saline, pH 7.4) and a small aliquot was taken for protein analysis using the Micro BCA Protein Assay (Pierce Biotechnology, Inc., Rockford, Ill.). Forty microliters of plasma microparticles and an equivalent amount of protein from the platelet MPs, resuspended with PBS to 40 μL, were mixed with 10 μL of 5× SDS-PAGE loading buffer (0.5 M Tris, pH 6.8, 10% SDS, 38% glycerol, 0.1% bromophenol blue). The separate samples (50 μL each) were heated to 95° C. for 5 minutes, allowed to cool to room temperature, and centrifuged for 2 minutes at 14,000 rpm prior to loading onto the gel. Microparticle proteins were electrophoresed approximately 1 cm into a 7.5% acrylamide SDS-PAGE using a Mini-gel system (Biorad, Hercules, Calif.) at 150 V. The acrylamide gel section containing the proteins was cut out and placed in fixative (50% methanol, 12% acetic acid, 0.05% formalin) for 2 hours. The in-gel tryptic digestion of the lanes and the peptide extraction was performed as previously described (see Shevchenko A, Wilm M, Vorm O, Mann M. Mass spectrometric sequencing of proteins silver-stained polyacrylamide gels. *Anal Chem.* 1996; 68: 850-858.). The extracted peptide solutions were lyophilized and reconstituted to 20 μL with 0.1% acetic acid for mass spectrometry analysis. Three sets of platelet- and plasma-derived MP peptides were generated, and each of these samples was analyzed by LC/MS twice.

ICAT-Labeling, electrophoresis, digestion, and peptide enrichment Relative quantitation of proteins following ICAT labeling was performed as depicted in FIG. 1B. Briefly, platelet- and plasma-derived microparticle pellets were resuspended in PBS (Phosphate buffered saline, pH 7.4), and protein concentration was determined. Solutions containing equivalent protein amounts of paired samples (plasma MP and platelet-derived MP) were lyophilized and resuspended in 1% SDS in denaturing buffer. Samples were labeled and processed using an ICAT labeling kit (Applied Biosystems, Foster City, Calif.) as instructed with the following modifications.

The initial labeling reaction was done at ½ of the recommended volume, protein amount, and ICAT reagent because of the low amount of protein obtained from each plasma MP preparation. The differentially-labeled proteins were mixed, applied to the gel, electrophoresed, and cut from the gel as described above except the loading buffer did not contain the reducing agent or SDS. The proteins were digested with trypsin, extracted from the gel and processed through the avidin column as recommended by manufacturer. The samples were lyophilized and reconstituted to 20 μL with 0.1% acetic acid for mass spectrometry analysis. This procedure was repeated three times with plasma MPs labeled with the light ICAT reagent for two of these samples and labeled with the heavy ICAT reagent in the third.

Liquid chromatography/mass spectrometry (LC/MS) and protein identification. Samples were loaded onto a 360 μm o.d.×75 μm i.d. microcapillary fused silica precolumn packed with irregular 5-20 μm C18 resin. After sample loading, the precolumn was washed with 0.1% acetic acid for 15 minutes to remove any buffer salts or gel contaminants. The precolumn was then connected to a 360 μm o.d.×50 μm i.d. analytical column packed with regular 5 μm C18 resin constructed with an integrated electrospray emitter tip. Samples were gradient eluted with an 1100 series binary HPLC solvent delivery system (Agilent, Palo Alto, Calif.) directly into a ThermoFinnigan LTQ ion trap mass spectrometer (Thermo Electron Corp, San Jose, Calif.) at a flow rate of 60 nL/min. In another example, the samples were analyzed using a ThermoFinnigan LTQ-FT instrument, which provides superior mass resolution. The HPLC stepwise gradient used was initially 100% A, 5% B at 5 minutes, 50% B at 220 minutes, 100% B at 240 minutes, and restored to 100% A at 280 minutes (solvent A=0.1 M acetic acid, solvent B=70% acetonitrile in 0.1 M acetic acid). The LTQ mass spectrometer was operated in the data-dependent mode in which first an initial MS scan recorded the mass to charge (m/z) ratios of ions over the mass range 300-2000 Da, and then the 10 most abundant ions were automatically selected for subsequent collisionally-activated dissociation and an MS/MS spectrum recorded.

All MS/MS data were searched against a human protein database downloaded from the NCBI website using the SEQUEST® program (Thermo Electron Corp.). For unlabeled peptides, a static modification of 57 Da for cysteine residues was employed in the search parameters. For ICAT-labeled peptides, a static modification of 227.127 was used for the light isotope label and an additional 9 Daltons for the heavy ICAT-labeled peptides. Peptide identifications were made using a first-pass filtering of standard criteria as previously described (see Washburn M P, Wolters D, Yates J R, 3rd. Large-scale analysis of the yeast proteome by multidimensional protein identification technology. *Nat Biotechnol.* 2001; 19: 242-247), including cross correlation values $\geq 2.0$ (+1 charge), 2.2 (+2 charge) and 3.5 (+3 charge) and all peptides must be fully tryptic. Protein assignments required at least 2 MS/MS spectra matches that passed the above criteria. Manual validation of at least one MS/MS spectrum-peptide sequence match per protein was performed for all proteins that were determined to be differentially expressed.

Comparative analysis of unlabeled peptides using Spectral Count. For the unlabeled scheme (FIG. 1A), all search results not passing the quality criteria described above were eliminated. The number of spectra for each peptide was determined, and the number of total proteins detected were calculated. If any protein had a spectral count of less than 2 for either the plasma MPs or the platelet MPs, it was eliminated from that group. Only proteins with an overall spectral count of 10 or greater were analyzed further by this method. The ratio of spectra from the plasma MP versus the platelet MP was calculated, log 2 transformed, and then adjusted for an overall ratio score of 0.00 excluding peptides derived from vWF. The standard deviation (SD) of the log score was calculated, and all proteins that were over 3 SD above (or below) the mean were considered to be enriched (or depleted) with "high confidence". Proteins with log 2 scores between 2 and 3 SD greater than the mean were classified as possible candidates that should be examined further.

Figure 2:
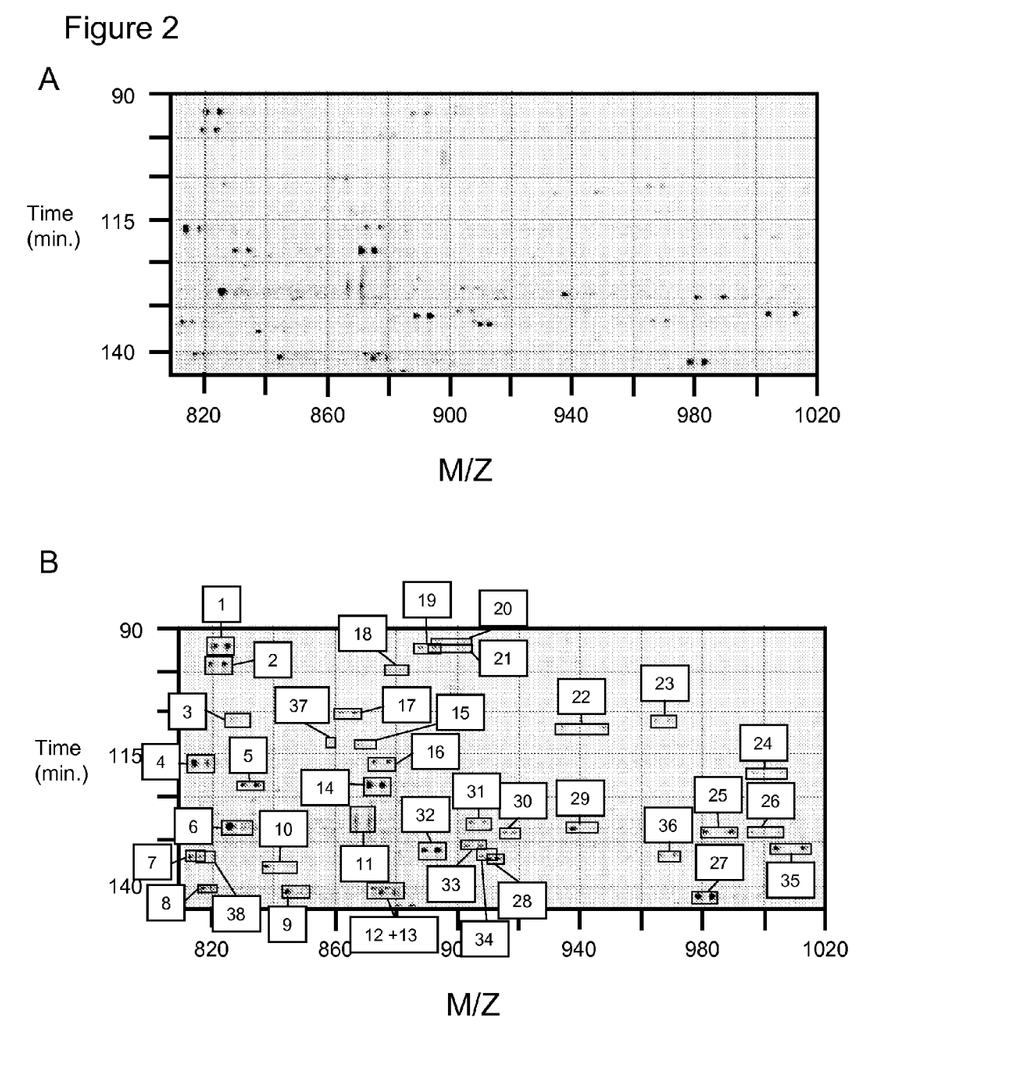

Comparative analysis of ICAT-labeled peptides using MSight®. Comparative quantitation was performed using MSight®, freely available from the Swiss Institute of Bioinformatics Expasy website. Data files (.RAW) generated using XCalibur Software (Thermo Electron Corp.) were converted to mzXML files using ReaDW (Institute for Systems Biology, Seattle, Wash.). These files were imported into MSight®, and the peptides were manually quantified. The peptides were identified using SEQUEST® as described above. A sample representation of the MSight® display for a small portion of one of these runs is shown in FIG. 2 (ion intensities not shown). Peptides that were detected in all three ICAT analyses based on SEQUEST® results were quantified, if possible. Then, peptides with high ion intensities were quantified and linked backed to SEQUEST® results. Attempts to quantify peaks sometimes failed due to poor signal-to-noise ratios, overlapping peptides, and ambiguous identification of a given peak.

Unless otherwise noted, ICAT quantitation results are only reported if good peak quantitation was possible in at least two of the three ICAT runs and labeled alternatively in these two runs. This led to the quantitation of 94 peptides. Utilizing the differential labeling, the ratios of the relative quantitation in plasma MPs versus platelet MPs were calculated, a log 2 transformation of these ratios was performed, and adjusted to generate an overall log 2 score of 0.00, excluding vWF. VWF was excluded because it was evident that there was significant enrichment in the plasma MPs and due to the large number of peptides examined for this protein and the extent of enrichment. To determine significance, the paired t-test was used to examine differences in peptide expression intensities between plasma MPs and platelet MPs. $P<0.05$ was used to determine differentially expressed peptides.

Results

Relative Quantitation of Plasma MPs and Platelet MPs using Spectral Counts. Plasma MPs and platelet MPs were isolated from three individuals, the proteins processed and digested into peptides, and peptide analysis of each was performed in duplicate. The MS/MS spectrum was searched using SEQUEST® and any spectrum not passing first-pass filtering was discarded. From the plasma MP, 1343±589 spectra per run (total of 8058 spectra in 6 runs) were obtained, identifying 3726 unique peptides and 550 unique proteins with 2 or more spectra (not shown). From platelet MPs, we obtained 2087±812 spectra per run (total of 12,522 spectra in 6 runs), identifying 6975 unique peptides and 1004 unique proteins with 2 or more spectra (results not shown).

Figure 3:
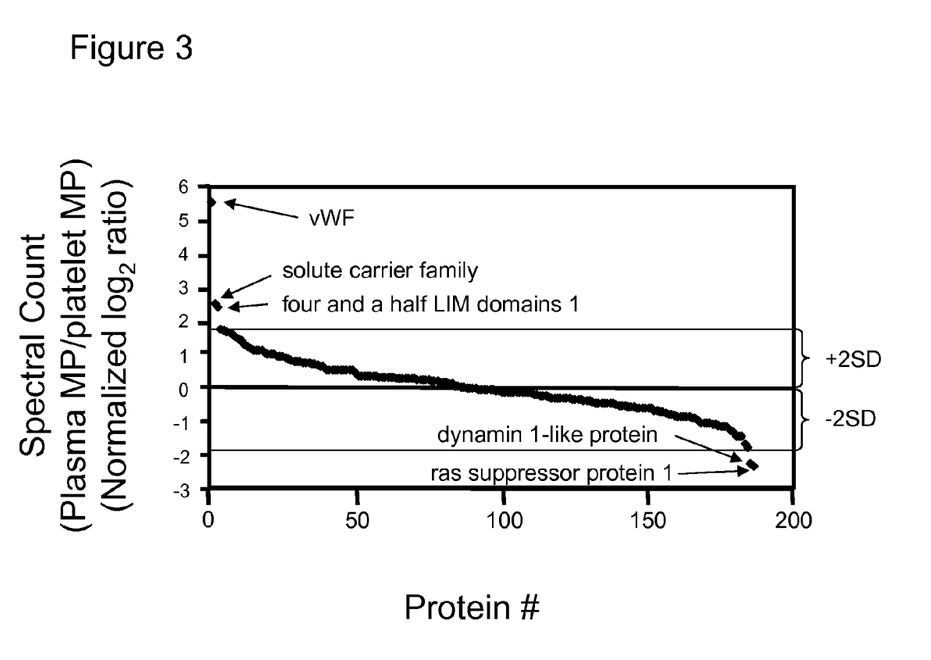
FIG. 3 represents a graphic illustration of a spectral count for 186 proteins from plasma-derived MPs and Platelet MPs. Log 2 of spectral count in plasma microparticles divided by spectral count in platelet microparticles for 186 unlabeled proteins. Proteins with peptides only present in plasma MPs are not shown but are included in Table 1. Five differentially expressed proteins are noted.

For proteins with a cumulative spectral count of 10 or more, the relative spectral counts were compared between plasma MPs and platelet MPs (results not shown). The log 2 of the ratio of the spectral counts was normalized to an average of 0.00 (excluding vWF) which represents the null hypothesis of equal representation of proteins in plasma and platelet MPs. FIG. 3 illustrates the normalized log 2 ratios for all proteins whose peptides were detected in both platelet and plasma MPs. In addition, there were 23 proteins for which peptides were detected in plasma MPs but not platelet MPs (see Table 1 below), all with high confidence (over 3 standard deviations away from mean). One of these, von Willebrand Factor (vWF), is clearly overexpressed in plasma MPs (over 3 standard deviations above platelet microparticles, 745 scans in plasma MP vs 23 scans in platelet MPs). The other two appeared to be overexpressed (with lower confidence—between 2 and 3 standard deviations away from mean) and we attempted to examine these further using ICAT-label (see section entitled "ICAT quantitation of Differentially Expressed Peptides based on Scan Number"). We showed with high confidence that a total of 24 proteins are enriched in plasma MPs versus platelet MPs. Complete description of these proteins and the peptide sequences detected were determined (results not shown). No proteins enriched in platelet MPs with high confidence were found.

| Protein Name | Accession No. | Plasma MP total scans | Plasma MP Peptides | Platelet MP total scans | Platelet MP Peptides | Spectral Count | plasma MP platelet MP |
|---|---|---|---|---|---|---|---|
| Fc fragment of IgG binding protein | 4503681 | 167 | 54 | 0 | 0 | 167 | — |
| complement component 4 binding protein, alpha | 4502503 | 114 | 23 | 0 | 0 | 114 | — |
| haptoglobin-related protein | 45580723 | 86 | 19 | 0 | 0 | 86 | — |
| complement component 4B | 4502501 | 86 | 37 | 0 | 0 | 86 | — |
| galectin 3 binding protein | 5031863 | 68 | 18 | 0 | 0 | 68 | — |
| apolipoprotein B-100 | 4502153 | 37 | 25 | 0 | 0 | 37 | — |
| alpha-2-macroglobulin | 4557225 | 36 | 21 | 0 | 0 | 36 | — |
| Haptoglobin | 4826762 | 32 | 12 | 0 | 0 | 32 | — |
| apolipoprotein A-I | 4557321 | 28 | 10 | 0 | 0 | 28 | — |

-continued

| Protein Name | Accession No. | Plasma MP total scans | Plasma MP Peptides | Platelet MP total scans | Platelet MP Peptides | Spectral Count | plasma MP platelet MP |
|---|---|---|---|---|---|---|---|
| CD5 antigen-like protein | 5174411 | 24 | 14 | 0 | 0 | 24 | — |
| Protein S, alpha | 4506117 | 24 | 15 | 0 | 0 | 24 | — |
| transferrin receptor | 4507457 | 20 | 14 | 0 | 0 | 20 | — |
| propionyl-Coenzyme A carboxylase, alpha | 4557833 | 18 | 1 | 0 | 0 | 18 | — |
| apolipoprotein E3 | 4557325 | 17 | 10 | 0 | 0 | 17 | — |
| immunoglobulin J chain | 21489959 | 15 | 5 | 0 | 0 | 15 | — |
| complement component 4 binding protein, beta | 4502505 | 14 | 5 | 0 | 0 | 14 | — |
| brain adenylate cyclase 1 | 31083193 | 12 | 1 | 0 | 0 | 12 | — |
| transferrin | 4557871 | 11 | 8 | 0 | 0 | 11 | — |
| complement component 3 | 4557385 | 11 | 10 | 0 | 0 | 11 | — |
| Ig kappa chain | 51475407 | 10 | 2 | 0 | 0 | 10 | — |
| apolipoprotein C-III | 4557323 | 10 | 2 | 0 | 0 | 10 | — |
| tenascin C | 4504549 | 10 | 9 | 0 | 0 | 10 | — |
| coagulation factor VIII | 4503647 | 10 | 10 | 0 | 0 | 10 | — |
| von Willebrand factor* | 4507907 | 745 | 102 | 23 | 15 | 768 | 32.39 |
| solute carrier family 4, anion exchanger, member 1* | 4507021 | 12 | 7 | 3 | 3 | 15 | 4.00 |
| four and a half LIM domains 1* | 21361122 | 11 | 4 | 3 | 1 | 14 | 3.67 |

*in plasma-derived compared to platelet-derived microparticles.

Figure 4:
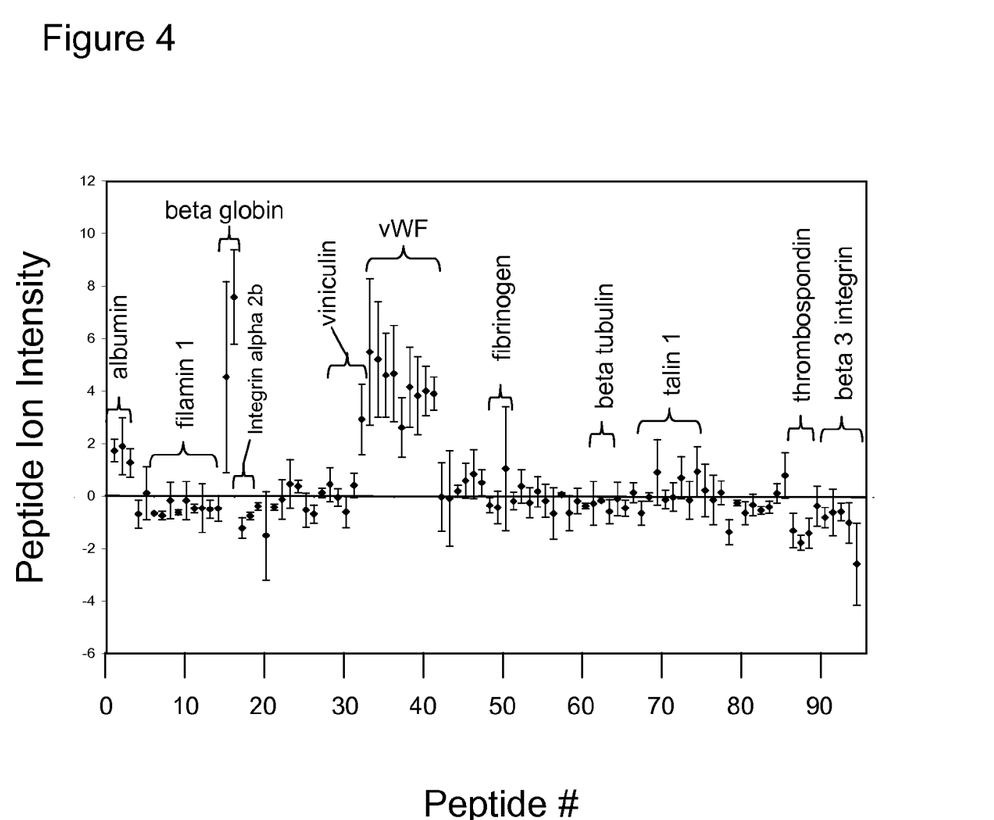
FIG. 4—a graphic representation of relative ion intensities for 94 peptides from plasma-derived MPs and platelet MPs following ICAT labeling. Normalized Log 2 of adjusted ion intensities for 94 peptides. Peptides from selected proteins are denoted.

Quantitative Analysis of Plasma MPs and Platelet MPs using ICAT As a complementary approach to examine differences in the protein composition of platelet MPs versus plasma MPs, a differential analysis using isotope labeling was performed. MP were differentially labeled and mixed prior to PAGE, trypsin digestion, extraction, and LC/MS (FIG. 1B). This was performed three times, and 94 of the more abundant peptides were quantified (results not shown). The log 2 of the ratios of the peptide abundances in plasma MPs to platelet MPs was calculated, and the average adjusted to 0.00, excluding the peptides from vWF (FIG. 4). Expression of peptides from three proteins (albumin, beta globin, and vWF) were consistently enriched in plasma MPs versus platelet MPs. The results for vWF are consistent with those obtained from spectral count analysis. While the spectral counts for albumin and beta globin (and several other hemoglobin proteins) were all about 2-fold higher in the plasma MPs versus the platelet MPs, the prior method was not quantitative enough to demonstrate an enrichment.

Peptides from three proteins, thrombospondin, and integrins alpha 2b and beta 3, that are normally associated with platelet function, appear to be enriched in the platelet MP. Peptides from more ubiquitous proteins, such as the cytoskeletal proteins, do not show such enrichment. One possible explanation could be that when platelet MPs are in the plasma, they could lose certain proteins either by degradation, cleavage, or binding to surfaces. It seems unlikely that it is caused simply by the presence of MPs from other sources because even if 20% of the MPs were not of platelet origin, that would not lead to a sufficient dilution of signal to be detected by this method.

ICAT quantitation of Differentially Expressed Peptides based on Scan Number In order to confirm the results of the spectral count analysis of unlabelled proteins, the peptides from all proteins (except vWF) which were determined to be enriched in one fraction based on spectral count analysis were examined (results not shown). Of these 27 proteins, spectra for peptides from 16 of these were detected in at least one of the three ICAT analysis. Similar to the spectral count of the unlabelled samples, there was a dramatic difference in spectral counts of the ICAT-labeled proteins between the two samples for these "enriched proteins" with 63 spectra for peptides from these proteins in the plasma MPs while only 2 were detected in the platelet MPs (results not shown). Of the 63 Peptides identified by Sequest, the ion intensities of 33 (representing 27 different) peptides could be quantified. It is important to note in many cases, the peptide from the platelet microparticle sample was not visually detected and the background ion intensities was used. This likely led to an underestimation of the fold enrichment in plasma MPs. This is particularly true for a number of peptides that had poor signal-to-noise ratios due to low abundance. Peptides from all of the proteins believed to be enriched in the plasma MP had an adjusted log 2 score of over 1.58, representing at least a three fold increase in concentration. Dynamin 1-like protein, which was enriched in the platelet MP had a log 2 score less than 0.00, suggesting that it truly is enriched in the fraction.

Discussion: Comparing the results from the two approaches (spectral counts versus ICAT-label) provides us with a wealth of information about the relative strengths and weaknesses of each. The most obvious strength of the spectral count approach is its ability to generate a large number of protein differences without extensive and time consuming manual quantitation. The main strength of the ICAT based approach is its superior quantitation; being able to detect 2-fold differences in abundance. While it is currently extremely time consuming to determine these differences, the development and availability of better software should alleviate this problem. It is interesting to note that spectral count appears to work for lower abundant peptides/proteins even when the ion current does not appear above the background. These features demonstrate the complementary nature of the two approaches.

Analysis of microparticles isolated from healthy volunteers shows 24 gene products enriched in plasma MPs compared to platelet microparticles isolated from the same individuals. Peptides from twenty three of these, represented by a total of 860 mass spectra and 325 peptides, were not detected in platelet MPs. Beyond statistical analysis, confidence in the detected differences is further enhanced by confirmation using direct ICAT-based comparison. The present study, for the first time, defines the protein composition of plasma microparticles as compared with platelet-derived microparticles using LC/MS as an unbiased approach. As expected, 186 of 209 gene products identified in plasma MPs are also found in platelet microparticles and platelets, confirming that most plasma MPs are derived from platelets. However, we found significant and potentially biologically important differences. Almost all (23 of 24) differentially expressed gene products as determined by spectral count were found exclusively in plasma-derived and not in platelet-derived MPs. Several lines of reasoning suggest that contamination with plasma proteins is not a major factor. First, of the most abundant plasma proteins, albumin, IgG, transferrin, fibrinogen, and IgA, only one, transferrin, was enriched in the plasma MPs versus the platelet MPs based on spectral counts and this protein had a relatively low number of these counts (109th most abundant protein). Its receptor, a membrane protein, presumably in exosomes (see below) had almost double the spectral counts. Second, the plasma-derived proteins detected in the plasma MPs are not a random collection as would be expected if it was a contaminant. For example, seven of these proteins are associated with apoptosis of cells. Four of them, complement 3, complement 4B, complement 4 binding proteins α and β, are from the complement pathway.

One mechanism by which nucleated cells are resistant to complement-induced cell death is by shedding the complement components off of the membrane. The complement components detected in our study could represent MPs generated by subclinical autoimmune processes. Complement C3 is the most important complement component that can be activated by any of the three distinct pathways, classical (antibody-initiated), lectin (microbe-initiated) and alternative pathways. The most likely explanation is subclinical activation of the classical pathway, which includes C3 and C4, by autoantibodies. Subclinical levels of autoantibodies are widely found in healthy individuals. Some of them include so-called natural antibodies, for example, to blood group antigens. Others are against certain pathogens such as *Streptococcus pneumoniae* and cross-react with endogenous oxidized lipids such as oxLDL. However, C4 is involved in both the lectin and classical pathways, so we cannot exclude that intestinal or other commensal flora may provide a stimulus for subclinical complement activation that leads to expulsion of the complement-bound membranes into microparticles. C4BP (C4 Binding protein) is a potent circulating soluble inhibitor that inhibits both the classical and alternative pathway with a role in localizing complement regulatory activity to the surface of apoptotic cells, which undergo ectocytosis to release MPs. Part of this complex includes Protein S, another protein enriched in the plasma MPs which has been independently shown to stimulate the phagocytosis of apoptotic cells.

Two other proteins enriched in plasma MPs, CD5-like antigen and galectin 3-binding protein also are associated with inhibition of apoptosis. CD5-like antigen, also called SP-α, has not been extensively studied, but its mouse homolog, AIM (apoptosis inhibitor in macrophages) has several informative studies (see Joseph S B, et. al., *Cell*. 2004; 119: 299-309; and Miyazaki T, et. al., *J Exp Med*. 1999; 189: 413-422). Cells from mice deficient in liver X receptors (LXRs) undergo accelerated apoptosis when challenged with *Listeria monocytogenes*, which is highly dependent on the AIM, a direct target for regulation by LXRα. Similarly, thymocytes have been shown to have increased susceptibility to apoptosis in mice lacking AIM. Galectin 3-binding protein, also called Mac-2 binding protein, associates with galectin 3, which increases cellular resistance to apoptosis. The presence of all these proteins in plasma MPs suggests that a larger percentage of these particles are either derived from apoptotic cells or an indication that microparticles are shed to prevent apoptosis.

Another set of proteins associated with plasma MPs are related to iron transport and hemoglobin clearance: transferrin, transferrin receptor, haptoglobin, and haptoglobin-related protein. Therefore, its presence in the plasma microparticles, along with its ligand, transferrin, is logical. Haptoglobin is an abundant protein that binds free hemoglobin which would otherwise be toxic to cells, especially in the kidney. Hemoglobin was detected by our analysis in both plasma MPs and platelet MPs, suggesting that haptoglobin-hemoglobin complexes may associate with MPs. It is not known why haptoglobin and haptoglobin-related proteins are overexpressed in plasma MPs.

The third category of plasma proteins overexpressed in plasma MPs are immunoglobulins, represented by immunoglobulin (Ig) J chain and kappa chain. This is not a random selection of immunoglobulins, again making plasma contamination a less likely explanation. IgJ is associated with IgM, which includes all natural antibodies. Also enriched are several complement components, as discussed above. These findings are consistent with our idea that the classical complement pathway may be activated at a low level through IgM auto-antibodies, leading to the formation of microparticles from unknown cells (not platelets) that remove IgJ and associated complement components from the affected cell membrane.

Four proteins found herein to be overexpressed in plasma MPs compared to platelet MPs, are associated with lipoproteins (results not shown). Unlike the others described above, these most likely represent contamination of plasma MPs with the larger plasma lipoproteins of the chylomicron (apo A-I and C-III), chylomicron remnant (apo E), VLDL (apo A-I, B100, and C-III) and IDL (apo B100 and E) fractions. Plasma lipoproteins appear in overlapping fractions with microparticles, because their sizes and therefore, their gel filtration properties are similar to MPs (results not shown). While they should remain in the supernatant after the final centrifugation step, their contamination with the pellet is difficult to avoid. In addition to the four lipoproteins found overexpressed in plasma microparticles, apolipoproteins A-II, C-II, L-I, and Lp(a), were found in only the plasma MPs but the number of spectra for each was below 10, and were not examined further. Three proteins associated with blood coagulation, protein S, factor VIII, and vWF (data not shown), were enriched in plasma MPs compared to platelet MPs.

vWF in platelet MPs being highly enriched in plasma MP as disclosed herein was unexpected, suggesting that endothelial vWF associates with plasma MPs or even promotes their formation. Endothelial vWF is secreted from Weibel-Palade bodies and previously has been shown to be present in endothelial-derived MPs under disease conditions. It exists as a very large multimer and is cleaved by MMP-13. Our proteomic analysis does not distinguish between monomers and multimers. The association of coagulation factors and platelet-binding factors is entirely consistent with the idea that plasma MPs are a pro-coagulant surface and associate with nascent thrombi.

FCGBP is a protein with unknown function produced by intestinal and colonic goblet cells. Due to its cellular source and its ability to bind IGG, it has been hypothesized to assist in preventing antigen invasion into the mucosa. Kobayashi et al. found that FCGBP could inhibit a complement-mediated reaction and suggested that it may play an important role in immunological defense of mucosal surfaces (see *Gut.* 2002; 51: 169-176). While this goes along with our theories of ectosome production discussed above, there is little evidence to support the connection between FCGBP and the prevention of cell death in vascular tissue. This is particularly true considering the location of FCGBP production. However, the detection of this protein in plasma MPs is very intriguing especially when one considers its prevalence (spectral count of 167 including 54 unique peptides).

Among the remaining three proteins, propionyl-coenzyme A carboxylase alpha and brain adenylate cyclase are intracellular proteins, while tenascin is an extracellular matrix protein. Propionyl-coenzyme A carboxylase is a mitochondrial enzyme involved in the catabolism of amino acids, odd-chained fatty acids and other metabolites. Tenascin is an extracellular matrix protein associated with provisional and tumor matrices but not found in most mature tissues. Tenascin may be secreted at sites of small injuries and wound healing, and cells with rapid turnover such as leukocytes and wound fibroblasts may shed tenascin associated with MPs. Alternatively, tenascin may form aggregates that migrate in the MP fraction. All three of these three proteins were unexpected in the plasma MP fraction. Further studies are needed to examine their implications. However, they are clearly not a random assortment of plasma protein contaminants.

In conclusion, the present disclosure establishes significant differences between plasma- and platelet-derived microparticle proteins. A large majority of these differences are proteins involved with apoptosis or iron transport. It is reassuring that very few proteins were detected in plasma MPs that could be classified as plasma contaminants. In studying the biology of complement, coagulation and other processes, microparticles will now have to be considered as important contributors for removing such components from cells. It remains to be seen if there are dramatic differences under pathological conditions and is the next step in determining their importance in a wide variety of diseases.

Candidate Biomarkers for Arthritis

The above-described procedures were used to identify candidate arthritis biomarkers. Blood samples were drawn from five patients matched for age, smoking, gender, and risk factors. One patient, the case, had arthritis. This patient's sample was analyzed in duplicate and compared to the other four, also analyzed in duplicate. The proteins shown in Table 2 below are significantly overexpressed in the case as determined by a stringent statistical test (Student's T test followed with Bonferroni correction for multiple comparisons) compared to the controls (i.e., other patients). Proteins that are associated with known problems of blood drawing such as hemolysis were removed. An example of a removed protein is SPTB spectrin beta isoform a, a protein mainly found in red blood cells and known to be associated with hemolysis, a common occurrence in blood sampling. The column "Bonferroni" contains the Bonferroni-corrected p-values (cutoff at 0.01). All of the shown proteins are positive biomarkers (i.e., they are higher when arthritis is present). Negative biomarkers, i.e., proteins that are detected less in the diseased sample, were removed for the purposes of this analysis. An example of a negative biomarker that was removed is STXBP2 Syntaxin-binding protein 2, which was found 0 times in the case and 9 times in controls. Negative biomarkers may still be useful, but positive biomarkers are often more desirable.

TABLE 2

| Protein | Accession | Bonferroni-corrected p | ratio disease/control |
| --- | --- | --- | --- |
| Isoform Gamma-B of Fibrinogen gamma chain precursor | 21891 | 0.0000002 | 4 |
| CATSPER3 cation channel, sperm associated 3 | 256795 | 0.0005068 | 16 |
| Alpha-1-acid glycoprotein 1 precursor | 22429 | 0.0006064 | 16 |
| Isoform 2 of WD repeat protein 1 | 216256 | 0.0009691 | 7 |
| MARK3 Isoform 1 of MAP/microtubule affinity-regulating kinase 3 | 183118 | 0.0012696 | 14 |
| SPTB spectrin beta isoform a | 784382 | 0.0013030 | 14 |
| Zyxin | 20513 | 0.0013883 | 9 |
| PDZ and LIM domain protein 1 | 10414 | 0.0013967 | 4 |
| RHOC Rho-related GTP-binding protein RhoC precursor | 27434 | 0.0015415 | 8 |
| DEFA1; LOC653600; LOC728358 Neutrophil defensin 1 precursor | 5721 | 0.0015895 | 14 |
| EPHB2 Isoform 1 of Ephrin type-B receptor 2 precursor | 21275 | 0.0015895 | 14 |
| ACTR3B actin-related protein 3-beta isoform 1 | 7068 | 0.0096585 | 8 |

Other methods which were used but not described herein are well known and within the competence of one of ordinary skill in the art of cell biology, molecular biology, biochemistry, analytical chemistry, bioinformatics and statistics. The invention should not be construed to be limited solely to the assays and methods described herein, but should be construed to include other methods and assays as well. One of skill in the art will know that other assays and methods are available to perform the procedures described herein. Headings are included herein for reference and to aid in locating certain sections. These headings are not intended to limit the scope of the concepts described therein under, and these concepts may have applicability in other sections throughout the entire specification. The disclosures of each and every patent, patent application, and publication cited herein are hereby incorporated herein by reference in their entirety. While this invention has been disclosed with reference to specific embodiments, it is apparent that other embodiments and variations of this invention may be devised by the previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

What is claimed is:

1. A method of identifying candidate biomarkers in the plasma microparticle sub-proteome, comprising:
   (a) isolating proteins from blood plasma microparticles obtained from at least one blood sample from a case and at least one blood sample from a control;
   (b) identifying the proteins;
   (c) applying a statistical test to measure the abundance of each protein identified; and,
   (d) determining the presence of positive and negative biomarkers by comparing the abundance of each protein identified in at least one case blood sample with the abundance of the same protein in at least one control blood sample.

2. The method of claim 1, wherein isolating proteins (a), further comprises:
   (e) isolating a plasma microparticle-enriched fraction from a blood sample;
   (f) purifying plasma microparticles from the enriched fraction; and,
   (g) isolating proteins from the purified microparticles.

3. The method of claim 2, wherein isolating a plasma microparticle-enriched fraction (e), comprises:
   (h) separating platelet-poor plasma (PPP) from a blood sample; and,
   (i) fractionating by size to obtain a plasma microparticle-enriched fraction.

4. The method of claim 3, wherein purifying plasma microparticles (f), comprises:
   (j) fractionating the plasma microparticle-enriched fraction to obtain plasma microparticles.

5. The method of claim 4, wherein isolating proteins (g), comprises:
   (k) delipidating the resulting plasma microparticles to obtain proteins.

6. The method of claim 2, further comprising:
   (l) optionally cleaving the resulting proteins to obtain peptides.

7. The method of claim 3, wherein (h) separating the plasma microparticle-enriched fraction is performed by centrifugation.

8. The method of claim 3, wherein (i) purifying by fractionating by size is performed by running the fractionated plasma microparticles through a size exclusion column.

9. The method of claim 4, wherein (j) fractionating the PPP is performed by centrifugation.

10. The method of claim 9, wherein the centrifugation is sufficient to form a pellet comprising: plasma microparticles.

11. The method of claim 5, wherein (k) delipidating is performed by submitting the plasma microparticles to gel electrophoresis.

12. The method of claim 11, wherein the gel electrophoresis is 1D SDS PAGE.

13. The method of claim 6, wherein (l) cleaving is performed by digesting the delipidated proteins with an appropriate enzyme.

14. The method of claim 13, wherein the enzyme is trypsin.

15. The method of claim 1, wherein (b) identifying is performed by sequencing the resulting proteins or peptides.

16. The method of claim 15, wherein (b) identifying is performed by sequencing the resulting peptides.

17. The method of claim 16, wherein the sequencing is performed by mass spectrometry.

18. The method of claim 17, wherein the sequencing is performed by a HPLC-MS/MS.

19. The method of claim 1, wherein (c) applying a statistical test is performed by using a method selected from: ion current, spectral count, and coverage.

20. The method of claim 19, wherein the statistical method used is comparing spectral counts between cases and controls.

* * * * *

(12) EX PARTE REEXAMINATION CERTIFICATE (9116th)
United States Patent
Ley et al.

(10) Number: US 7,462,489 C1
(45) Certificate Issued: Jul. 3, 2012

(54) METHODS FOR IDENTIFYING AND ANALYZING BIOMARKERS FROM PLASMA-DERIVED MICROPARTICLES

(76) Inventors: Klaus F. Ley, La Jolla, CA (US); David M. Smalley, Charlottesville, VA (US)

Reexamination Request:
No. 90/011,666, May 2, 2011

Reexamination Certificate for:
Patent No.: 7,462,489
Issued: Dec. 9, 2008
Appl. No.: 11/935,048
Filed: Nov. 5, 2007

Related U.S. Application Data

(60) Provisional application No. 60/857,928, filed on Nov. 9, 2006.

(51) Int. Cl.
*A01N 33/00* (2006.01)
*A01N 1/02* (2006.01)
*A01N 31/00* (2006.01)

(52) U.S. Cl. .................. 436/16; 514/1.1; 435/2; 436/86; 436/89

(58) Field of Classification Search .................. None
See application file for complete search history.

(56) References Cited

To view the complete listing of prior art documents cited during the proceeding for Reexamination Control Number 90/011,666, please refer to the USPTO's public Patent Application Information Retrieval (PAIR) system under the Display References tab.

*Primary Examiner* — Bruce Campell (57) ABSTRACT

The present invention provides methods for identifying candidate biomarkers in the plasma microparticle proteome. It also provides methods for isolating, identifying, and analyzing microparticles derived from plasma, particularly platelet-poor plasma.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-20 are cancelled.

\* \* \* \* \*

(12) EX PARTE REEXAMINATION CERTIFICATE (10656th)
United States Patent
Ley et al.

(10) Number: US 7,462,489 C2
(45) Certificate Issued: Jul. 10, 2015

(54) METHOD FOR IDENTIFYING AND ANALYZING BIOMARKERS FROM PLASMA-DERIVED MICROPARTICLES

(76) Inventors: Klaus F. Ley, La Jolla, CA (US); David M. Smalley, Charlottesville, VA (US)

Reexamination Request:
No. 90/011,666, May 2, 2011

Reexamination Certificate for:
Patent No.: 7,462,489
Issued: Dec. 9, 2008
Appl. No.: 11/935,048
Filed: Nov. 5, 2007

Reexamination Certificate C1 7,462,489 issued Jul. 3, 2012

Related U.S. Application Data (60) Provisional application No. 60/857,928, filed on Nov. 9, 2006.

(51) Int. Cl.
*A01N 33/00* (2006.01)
*A01N 1/02* (2006.01)
*A01N 31/00* (2006.01)
*G01N 33/68* (2006.01)

(52) U.S. Cl.
CPC ........ *G01N 33/6803* (2013.01); *G01N 33/6848* (2013.01); *G01N 2550/00* (2013.01); *Y10T 436/106664* (2015.01)

(58) Field of Classification Search
None
See application file for complete search history.

(56) References Cited

To view the complete listing of prior art documents cited during the proceeding for Reexamination Control Number 90/011,666, please refer to the USPTO's public Patent Application Information Retrieval (PAIR) system under the Display References tab.

*Primary Examiner* — Bruce Campell (57) ABSTRACT

The present invention provides methods for identifying candidate biomarkers in the plasma microparticle proteome. It also provides methods for isolating, identifying, and analyzing microparticles derived from plasma, particularly platelet-poor plasma.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-20 are cancelled.

\* \* \* \* \*